US00PP08941P

United States Patent [19]

Olesen et al.

[11] Patent Number: Plant 8,941

[45] Date of Patent: Oct. 18, 1994

[54] MINIATURE ROSE PLANT NAMED POULTUR

[75] Inventors: Mogens N. Olesen; Pernille Olesen, both of Fredensborg, Denmark

[73] Assignee: Bear Creek Gardens, Inc., Medford, Oreg.

[21] Appl. No.: 150,430

[22] Filed: Nov. 9, 1993

[51] Int. Cl.[5] ..... A01H 5/00

[52] U.S. Cl. ..... Plt./8.1

[58] Field of Search ..... Plt. 8.1

*Primary Examiner*—Howard J. Locker

*Attorney, Agent, or Firm*—Klarquist Sparkman Campbell Leigh & Whinston

[57] ABSTRACT

A miniature class rose plant having a uniform, compact growth habit; ease of propagation by softwood cuttings; long shelf life as a pot rose, and uniform white flower color.

1 Drawing Sheet

The present invention relates to a new and distinct variety of rose plant of the miniature class which was originated by us by crossing two unnamed seedlings.

The primary objective of this breeding was to produce a new rose variety with a good keeping quality as a pot rose having white flowers. The objective was substantially achieved, along with other desirable improvements, as evidenced by the following unique combination of characteristics that are outstanding in the new variety and that distinguish it from its parents, as well as from all other varieties of which we are aware:

1. Flowers of uniform white color;
2. Long shelf life as a pot rose;
3. Uniform, easy propagation from softwood cuttings; and
4. Compact and uniform habit of growth in 8 and 10 cm pots.

Asexual reproduction of this new variety by budding and by softwood cuttings, as performed at Fredensborg, Denmark, and Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of our new rose cultivar with color descriptions using terminology in accordance with The Royal Horticultural Society (London) Colour Chart, except where ordinary dictionary significance of color is indicated.

Parentage:

*Seed parent.*—An unnamed seedlng.

*Pollen parent.*—An unnamed seedling.

Classification:

*Botanical.*—*Rosa hybrida.*

*Commercial.*—Miniature.

FLOWER

Observations made from specimens grown in a garden environment in Fredensborg, Denmark, in 1991.

Blooming habit: Continuous.

Bud:

*Size.*—1.6 cm long when the petals start to unfurl.

*Form.*—Pointed ovoid.

*Color.*—When sepals first divide, bud color is White Group 155B. When half blown, the upper and lower sides of the petals are White Group 155B.

*Sepals.*—Color: Green Group 138B. Surface texture: Covered in fine hairs. There are three lightly appendaged sepals. There are two unappendaged sepals with smooth edges.

*Receptacle.*—Color: Green Group 138A. Shape: Pitcher. Size: Small (0.3 cm×0.3 cm). Surface: Smooth.

*Peduncle.*—Length: Short (3.80 cm). Surface: Smooth. Color: Medium green. Strength: Stiff, erect.

Bloom:

*Size.*—Small. Average open size is 3 cm in diameter.

*Borne.*—Several together, in rounded clusters of 2 to 5 flowers.

*Stems.*—Short (13 cm to 15 cm).

*Form.*—When first open: Globular. Permanence: Flattens, outer petals curl back in a quill fashion.

*Petalage.*—Number of petals under normal conditions: 20 to 40.

*Color.*—The upper and reverse sides of the petals are White Group 155B. The base of each petal is Yellow Group 2C. The major color on the upper side is White Group 155B.

*Variegations.*—None.

*Discoloration.*—The general tonality at the end of the first day: No change. At the end of the third day: No change.

*Fragrance.*—Slight.

Petals:

*Texture.*—Thick.

*Shape.*—Oval.

*Form.*—Tips are slightly recurved; edges are slightly quilled.

*Arrangement.*—Imbricated, with many petaloids in the center.

*Persistence.*—Drop off cleanly.

*Lastingness.*—On the plant: Very long (14 to 20 days). As a cut flower: Very long (10 days).

Reproductive parts:

*Anthers.*—Size: Medium. Quantity: Many. Color: Yellow. Arrangement: Regular around styles, mixed with petaloids.

*Filaments.*—Color: Yellow.
*Pollen.*—Color: Gold yellow.
*Styles.*—Color: Greenish yellow.
*Stigmas.*—Color: Greenish white.

Form: Bush.

Growth: Vigorous, dwarf.

Foliage:
*Number of leaflets on normal mid-stem leaves.*—5.
*Size.*—Small (6.4 cm long×3.8 cm wide).
*Quantity.*—Normal.
*Color.*—New foliage: Green Group 137C. Old foliage: Green Group 139A.

Leaflets:
*Shape.*—Pointed oval.
*Texture.*—Upper side: Smooth.
*Edge.*—Serrated.
*Serration.*—Small.
*Petiole rachis.*—Color: Green.
*Petiole underside.*—Smooth with an occasional prickle.
*Stipules.*—Medium, bearded.

*Disease resistance.*—Resistant to mildew and blackspot under normal growing conditions in a garden environment in Fredensborg, Denmark.

Wood:
*New wood.*—Color: Light green. Bark: Smooth.
*Old wood.*—Color: Green. Bark: Smooth.

Prickles:
*Quantity.*—Ordinary on main canes from base. Few on laterals from main canes.
*Form.*—Straight.
*Color when young.*—Green and red.

Small prickles:
*Quantity.*—Few on main stalks. Few on laterals.
*Color.*—Green.

We claim:

1. A new and distinct variety of rose plant of the miniature class, substantially as herein shown and described, characterized particularly as to novelty by the unique combination of its uniform, compact growth habit; ease of propagation by softwood cuttings; long shelf life as a pot rose, and uniform white flower color.

* * * * *

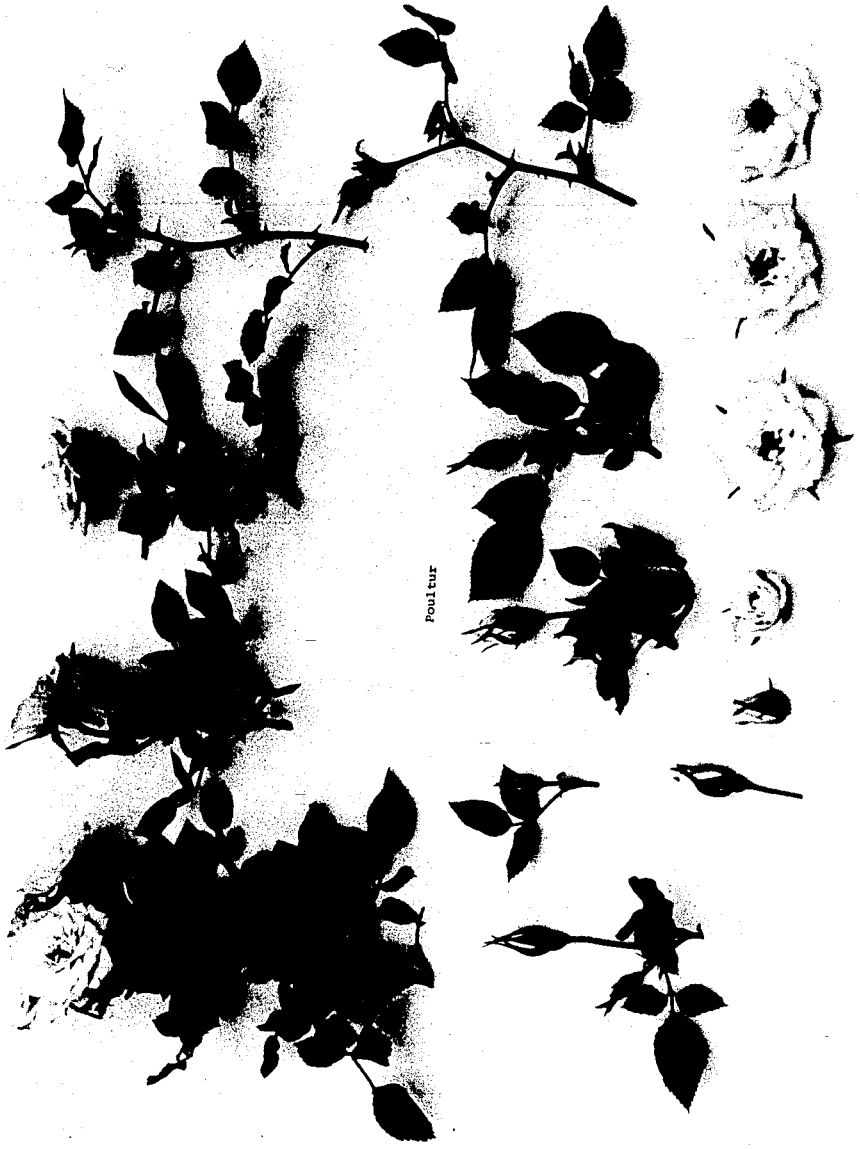
Poultur